(12) United States Patent
Watanabe

(10) Patent No.: US 7,309,159 B2
(45) Date of Patent: Dec. 18, 2007

(54) RADIATION IMAGING APPARATUS AND METHOD OF CONTROLLING THE SAME

(75) Inventor: Tetsuo Watanabe, Utsunomiya (JP)

(73) Assignee: Canon Kabushiki Kaisha, Tokyo (JP)

( * ) Notice: Subject to any disclaimer, the term of this patent is extended or adjusted under 35 U.S.C. 154(b) by 35 days.

(21) Appl. No.: 11/292,566

(22) Filed: Dec. 2, 2005

(65) Prior Publication Data

US 2006/0120512 A1    Jun. 8, 2006

(30) Foreign Application Priority Data

Dec. 3, 2004    (JP) .............................. 2004-351515

(51) Int. Cl.
*H05G 1/02* (2006.01)
(52) U.S. Cl. ...................................... 378/198; 378/117

(58) Field of Classification Search ................ 378/117, 378/114, 102, 195–198
See application file for complete search history.

(56) References Cited

U.S. PATENT DOCUMENTS 5,177,778 A * 1/1993 Tsurumaki et al. .......... 378/117
6,212,251 B1 * 4/2001 Tomura et al. ................ 378/15

FOREIGN PATENT DOCUMENTS

JP    11-99144    4/1999

* cited by examiner

*Primary Examiner*—Hoon Song
(74) *Attorney, Agent, or Firm*—Morgan & Finnegan, LLP

(57) ABSTRACT

In a radiation imaging apparatus having a radiation generator, an imaging unit including a detecting unit for detecting radiation to generate a radiation image data, a carriage for carrying the radiation generator, and an operating unit for providing an interface to a user, it is decided whether the radiation imaging apparatus is in a moving state or not. When it is decided that the radiation imaging apparatus is in a moving state, the operation function of the operating unit for the radiation detector and the imaging unit is limited.

4 Claims, 10 Drawing Sheets

FIG. 10A

|   | PATIENT NAME | SEX | ROOM | IMAGED PART | POSTURE | IMAGING |
|---|---|---|---|---|---|---|
| 1 | ○○△× | FEMALE | XXX | | | UNCOMPLETED |
| 2 | □□□□ | MALE | AAA | | | UNCOMPLETED |
| 3 | △△△ | MALE | YYY | | | UNCOMPLETED |
| ⋮ | ⋮ | | | | | |

FIG. 10B

|   | PATIENT NAME | SEX | ROOM | IMAGED PART | POSTURE | IMAGING | IMAGING |
|---|---|---|---|---|---|---|---|
| 1 | ○○△× | FEMALE | XXX | | | UNCOMPLETED | POSSIBLE |
| 2 | □□□□ | MALE | AAA | | | UNCOMPLETED | POSSIBLE |
| 3 | △△△ | MALE | YYY | | | UNCOMPLETED | NOT POSSIBLE |
| ⋮ | ⋮ | | | | | | |

US 7,309,159 B2

RADIATION IMAGING APPARATUS AND METHOD OF CONTROLLING THE SAME

CLAIM OF PRIORITY

This application claims priority from Japanese Patent Application No. 2004-351515 filed on Dec. 3, 2004, which is hereby incorporated by reference herein.

FIELD OF THE INVENTION

The present invention relates to a movable radiation imaging apparatus and a method of controlling the same.

BACKGROUND OF THE INVENTION

Conventionally, imaging apparatuses for irradiating an object with radiation, detecting the intensity distribution of radiation having passed through the object, and obtaining a radiation image data of the object have generally been used for industrial nondestructive inspections and medical diagnoses. As a typical imaging method of such imaging apparatuses, the film-screen method is available. In this method, radiation imaging is performed with a combination of a photosensitive film and a phosphor having a sensitivity to radiation. To be specific, a sheet of a rare-earth phosphor, which emits light in response to irradiation, is bonded and held on both sides of a photosensitive film, radiation having passed through a subject is transformed into visible light through the phosphor, and the light is captured by the photosensitive film. A latent image formed on the film can be visualized by development through a chemical treatment.

As digital technology has improved in recent years, the following method has become widely available: a radiation image is converted into an electric signal, the electric signal is subjected to image processing, and then the signal is reproduced on a CRT or the like as a visible image, so that a radiation image with high image quality can be obtained. For example, a radiation image recording/reproducing system is proposed in which a transmission image of radiation is temporarily stored in a phosphor as a latent image, and then the latent image is photoelectrically read by irradiation of excitation light such as laser light, so that a visible image is obtained.

Further, as semiconductor process technologies have improved in recent years, apparatuses for photographing radiation images using semiconductor sensors have been developed. These systems have a considerably wide dynamic range as compared with conventional radiation photographing systems using photosensitive films, and have a practical advantage of obtaining a radiation image not affected by fluctuations of the exposure amount of radiation. Further, unlike the conventional photosensitive film system, an output image can be obtained instantly without the need for a chemical treatment.

FIG. 9 is a conceptual diagram showing a system using such a radiation imaging apparatus 103. Radiation from a radiation generating device 101 is emitted to a subject 102, and radiation having passed through the subject reaches a radiation sensor 104 included in the radiation imaging apparatus 103. In the radiation sensor 104, radiation is transformed into visible light through a phosphor and detected as an electric signal by an photoelectronic converter arranged in a two-dimensional lattice. A control unit 105 is provided for controlling driving for reading, image transfer, and so on of the radiation sensor 104. The control unit 105 performs digital image processing on an image signal outputted from the radiation sensor 104, and displays the signal as a radiation image of the subject 102 on a monitor 106. The advantage of the system shown in FIG. 9 is that an image can be instantly monitored unlike the above radiation image reading/reproducing system which reads an image in post-processing. In such an imaging system, the radiation sensor 104 is set on a dedicated stand according to an imaging pattern such as a standing position or a lying position, and is properly set as necessary.

Conventionally, this kind of imaging apparatus has been placed and used in a radiation room. In recent years, however, a transportable imaging apparatus (called electronic cassette) has been developed with a small thickness and a light weight in order to attain faster and wide-range imaging. Thus, there is proposed an imaging system applicable to a round of visits as well as cassette imaging in a radiation room (see Japanese Patent Laid-Open No. 11-99144). Such an imaging system is quite useful because it is possible to solve the following problems: a number of cassettes have to be carried for storing conventional films and fluorescent screens during a round of visits, and imaging has to be performed again in the event of an imaging error which cannot be instantly confirmed.

The movable radiation imaging apparatus above requires, as a minimum, a battery which supplies electric power for generating radiation. Besides, in recent years, some imaging apparatuses include batteries capable of supplying electric power used for power for movement. When the electronic imaging apparatus above (e.g., electronic cassette) is used, more electric power is required and the capacity of the battery must be increased in order to drive the imaging apparatus. When a larger capacity battery is used, the weight and outer dimensions of the battery increase, adversely affecting the outer shape of the apparatus. Thus, such a large battery is unacceptable in view of operationality. However, when a small capacity battery is used, it must be charged very frequently, and the rate of operation may decrease.

When the mobile radiation imaging apparatus is moved, an operation unit may be carelessly touched and the apparatus may perform an unnecessary operation. Such an unnecessary operation wastes power. If persons to be imaged can be displayed on a list when the apparatus is moved, an examiner can conveniently confirm, for example, the next person to be imaged. However, when the overall apparatus is turned off while being moved, a list of persons to be imaged cannot be displayed on a display, thereby considerably degrading operationality. Therefore, in the case where the radiation imaging apparatus is moved while power is turned on, power conservation measures are desired for preventing an unnecessary operation caused by an operating error or the like and also reducing power consumption.

SUMMARY OF THE INVENTION

The present invention is devised in view of the foregoing problems. An object of the present invention is to suspend an unnecessary function to reduce the occurrence of an unnecessary operation caused by an operating error or the like when an apparatus is in a moving state and, by extension, to reduce power consumption.

In order to attain the object, a radiation imaging apparatus of the present invention is configured as follows. That is, according to one aspect of the present invention, there is provided a radiation imaging apparatus having a radiation generator, an imaging unit including a detecting unit for detecting radiation to generate a radiation image data, a carriage for carrying the radiation generator, and an operating unit configured to provide an interface to a user, the apparatus comprising: a decision unit configured to decide whether the radiation imaging apparatus is in a moving state or not, and a limiting unit configured to limit an operation function of the operating unit when the decision unit decides that the radiation imaging apparatus is in a moving state, the operating function for the radiation generator and the imaging unit.

Other features and advantages of the present invention will be apparent from the following description taken in conjunction with the accompanying drawings, in which like reference characters designate the same or similar parts throughout the figures thereof.

BRIEF DESCRIPTION OF THE DRAWINGS

The accompanying drawings, which are incorporated in and constitute a part of the specification, illustrate embodiments of the invention and, together with the description, serve to explain the principles of the invention.

FIGS. 10A and 10B are diagrams showing display examples of lists of management information in an operating unit.

DETAILED DESCRIPTION OF THE PREFERRED EMBODIMENTS

Preferred embodiments of the present invention will be described below with reference to the accompanying drawings. In these embodiments, a medical imaging apparatus (X-ray imaging apparatus) for imaging a subject (human body) by using X-rays will be described as an example of a radiation imaging apparatus of the present invention. The present invention is also applicable to an X-ray imaging apparatus for photographing a subject other than a human body or an imaging apparatus using other kinds of radiation (e.g., an electron beam and a gamma ray).

First Embodiment

Figure 1:
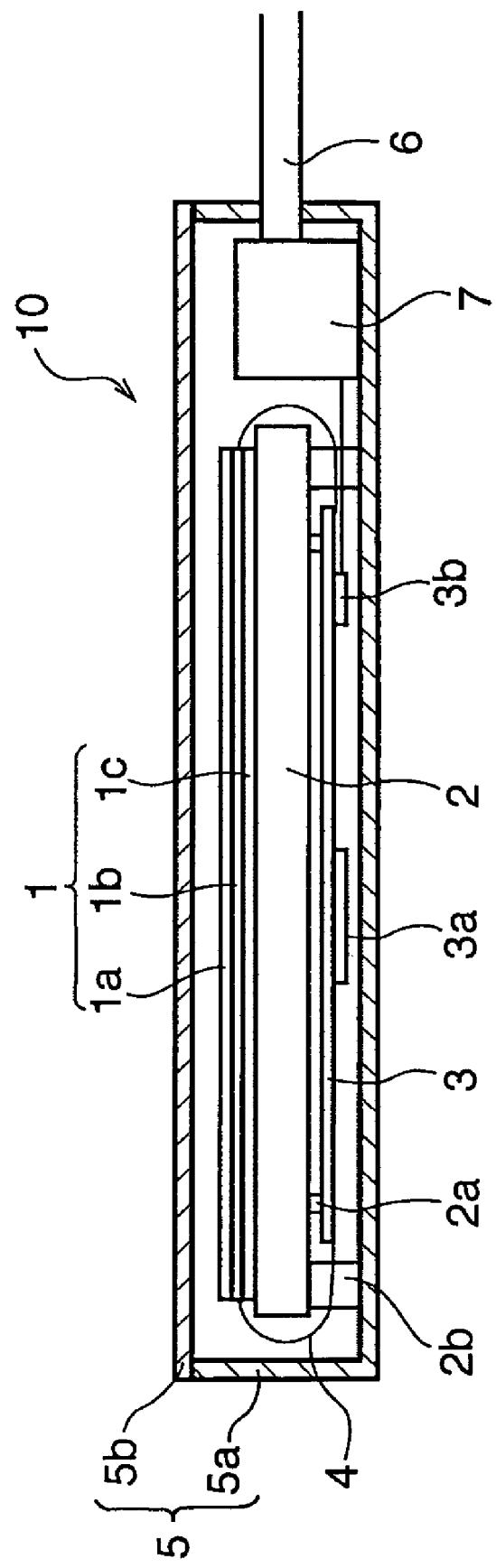
FIG. 1 is a side sectional drawing showing an imaging unit of a first embodiment.
Figure 2:
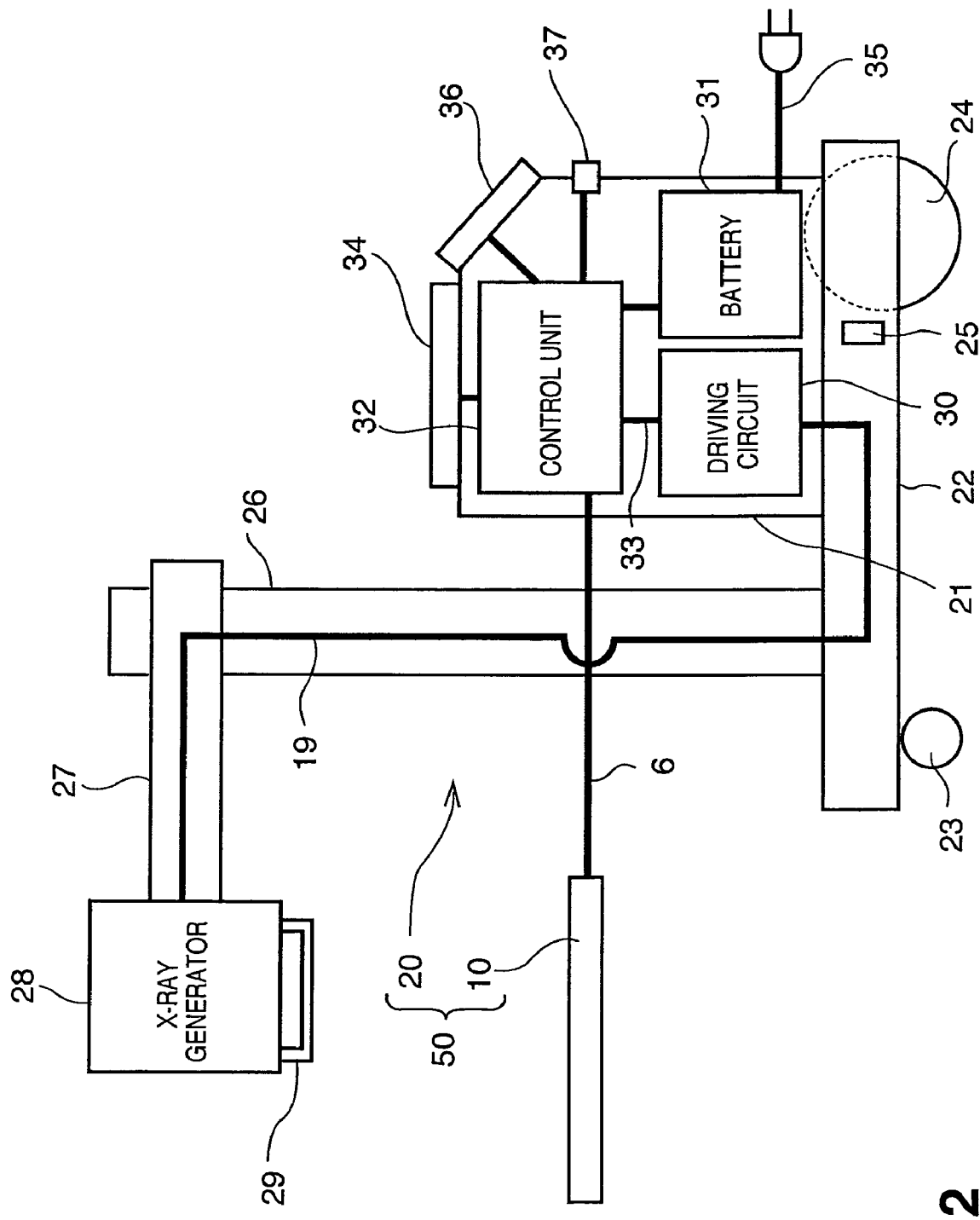
FIG. 2 is a diagram for explaining the configuration of a movable imaging apparatus according to the first embodiment.
Figure 3:
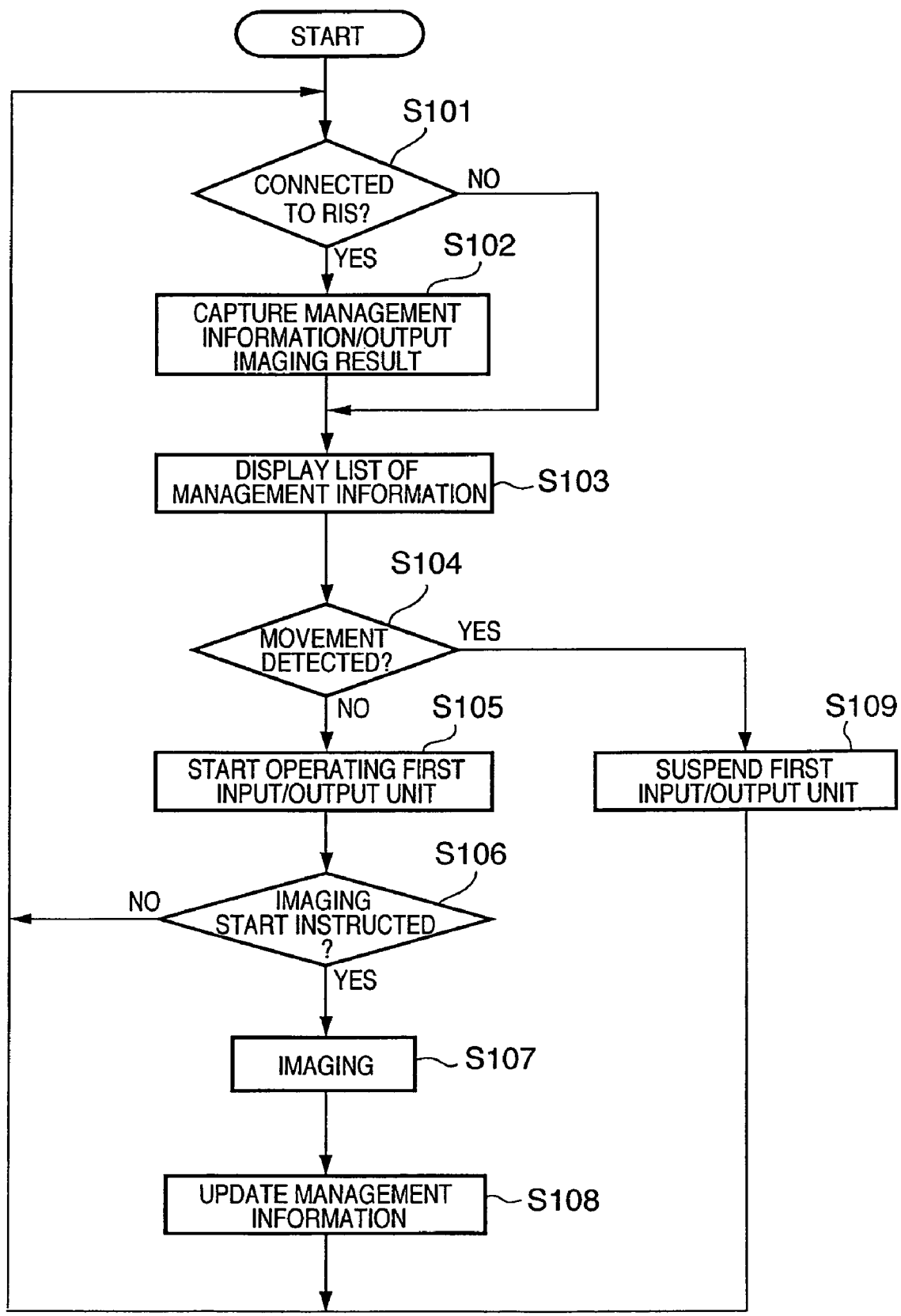
FIG. 3 is a flowchart for explaining the operations of the movable imaging apparatus according to the first embodiment.

FIG. 1 is a side sectional diagram showing an imaging unit of the present embodiment. FIG. 2 is a diagram for explaining the configuration of a movable imaging apparatus of the present embodiment. FIG. 3 is a flowchart for explaining the operations of the movable imaging apparatus of the present embodiment.

In FIG. 1, an X-ray detection panel 1 is mainly constituted of a fluorescent screen 1a, an photoelectronic converter 1b, and a substrate 1c. In many cases, the substrate 1c is a glass plate because the glass plate causes no chemical action with a semiconductor element, the glass plate is resistant to the temperature of a semiconductor process, and dimensional stability and so on are necessary. The photoelectronic converter 1b is formed in a two-dimensional array on the glass substrate 1c according to a semiconductor process. The fluorescent screen 1a is formed by applying a phosphor of a metal compound to a resin plate, and integrated with the substrate 1c by bonding.

The X-ray detection panel 1 configured thus is fixed and supported on a metal base 2 with a mechanical strength. A circuit board 3 has electronic parts 3a and 3b for processing an electric signal having been converted by the photoelectronic converter 1b. The circuit board 3 is connected to the photoelectronic converter 1b via a flexible circuit board 4 and fixed via protrusions 2a provided on the back of the base 2. The base 2 is fixed to a case body 5a via a supporting portion 2b and stored in a case 5 after being sealed with a case lid 5b having X-ray permeability, so that an imaging unit 10 is configured as an electronic cassette. Further, a cable 6 for supplying power and transmitting signals such as an image signal and a control signal to the circuit board 3 and so on is connected to the imaging unit 10 via a relay part 7 or the like.

The imaging unit 10 configured thus for a round of visits is combined with a movable X-ray generator 20 and used as a movable imaging apparatus 50. Referring to FIG. 2, the following will describe the configuration of the present embodiment.

A movable imaging apparatus body 21 is installed on a carriage 22 having a plurality of wheels 23 and 24. The apparatus body 21 can be freely moved. A rotation sensor 25 provided on the carriage 22 detects the rotation of the wheel 24, and the detection signal of the sensor 25 is used to detect whether the imaging apparatus 50 is in a moving state or not. The rotation sensor 25 can be implemented by a simple method including a rotary encoder. On the carriage 22, a column 26 is supported perpendicularly to the carriage 22 so as to rotate about its axis. Further, an arm 27 is provided which extends horizontally relative to the column 26 and is supported so as to slide in the vertical direction. An X-ray generator 28 including an X-ray vacuum tube is mounted on the arm 27 so as to horizontally slide along the arm 27 and rotate about the axial direction of the arm 27. With this configuration, the irradiation direction of X-rays from the X-ray generator 28 can be freely adjusted. The X-ray generator 28 comprises a grip 29. The grip 29 comprises a contact sensor (not shown). When the contact sensor detects that the grip 29 is held by the operator, a lock for prohibiting the movements of mechanisms including the arm 27 and the X-ray generator 28 is released, so that the X-ray vacuum tube can be set at a desired position and posture within the permissible range of the rotation and slide.

A driving circuit 30, a battery 31, and a control unit 32 are disposed in the body 21. The driving circuit 30 includes an electric circuit for controlling the driving of the vacuum tube for X-ray irradiation, the lock of the mechanism, and so on. The battery 31 supplies power to the units of the movable imaging apparatus 50. The control unit 32 controls the imaging unit 10 and the X-ray generator 28 to obtain, for example, a photographed image. The control unit 32 mainly comprises a storage part 321 for storing a photographed image obtained by performing digital processing on an image signal from the imaging unit 10, an interface 322 which drives first and second operating units 34 and 36 for providing an interface to the operator, the X-ray generator 28, and the imaging unit 10, and a controller 323 for controlling these parts. For example, the controller 323 comprises a CPU and memory. A control program stored in the memory is executed by a CPU, so that various kinds of control can be performed.

The control unit 32 instructs the driving circuit 30 through a cable 33 to generate an X-ray in the X-ray generator 28. The X-ray generator 28 and the driving circuit 30 are connected to each other via a cable 19, and a driving signal and power are supplied to the X-ray generator 28. The driving circuit 30 transmits the driving signal to the X-ray generator 28 in response to the instruction from the control unit 32 to generate an X-ray, so that exposure is controlled.

The driving timing of the X-ray detection panel 1 has to be controlled in synchronization with exposure from the X-ray generator 28. Thus, the imaging unit 10 is connected to the control unit 32 via the cable 6 and a driving signal is transmitted from the control unit 32 to the imaging unit 10 through the cable 6. The cable 6 is provided to supply power to the imaging unit 10 and transmit signals such as an image signal and a control signal to the imaging unit 10, and the cable 6 has flexibility not interfering with operations and has a sufficient length not interfering with power supply and signal transfer.

The first operating unit 34 used for the operations and so on of the imaging unit 10 and the movable X-ray generator 20 is composed of a monitor for display output and an input device for operation input, and the first operating unit 34 is disposed on the body 21 in the present embodiment. The input device includes, for example, a combination of a selection key for switching selected items on a monitor display and a decision button for determining a selection, and a touch panel or the like on a monitor screen. On the monitor of the first operating unit 34, an operation menu is displayed where an imaged part (a part to be imaged) is selected, the imaging unit 10 is changed to an imaging performable state, and imaging conditions such as the tube voltage, tube current, irradiation time, and so on of the X-ray generator 28 are set. These items on the operation menu are selected and set by the input device, and then desired imaging is performed. In other words, in the first operating unit 34, various settings are made for the imaging unit 10 and the X-ray generator 28 and an imaging operation is instructed. Processing such as trimming and rotation is performed on a photographed image, and a series of operations until the photographed image is stored in the storage part included in the control unit 32 can be performed using the input device of the first operating unit 34.

The battery 31 is connected to the driving circuit 30, the imaging unit 10, the control unit 32, and so on to supply power to each of the parts, and can be charged from the outside via an AC cable 35. Power for operating the movable imaging apparatus 50 is charged in the battery 31 beforehand through the AC cable 35 in a time period during which no imaging operation is performed. The AC cable 35 is stored in the apparatus body 21 when the apparatus 50 is moved.

A software module (management module) for managing information on patients for whom X-ray imaging is ordered and management information including the imaging conditions and the history of imaging is installed in the control unit 32. Such a management module may be implemented by a control unit different from the control unit 32. As shown in FIG. 2, the second operating unit 36 is connected to the control unit 32 and the management module displays a list of the management information (for example, a list of patients or the like) on the monitor of the second operating unit 36, so that the operator can confirm the contents of management. When a displayed list is placed out of one screen, the scrolling of the screen can be instructed through the input device provided in the second operating unit 36. These management information can be obtained through communications with an external terminal (not shown) of a hospital via an external communication connector 37 connected to the control unit 32. In this example, the external terminal is an RIS terminal connecting to a RIS (Radiology Information System). However, the system connecting the apparatus is not limited to the RIS. The apparatus may be connected to any other systems including an HIS (Hospital Information System). Such communication processing is also supported by the management module.

The following will describe the operations of the movable imaging apparatus 50. FIG. 3 is a flowchart for explaining the operations (the procedure of the control unit 32) of the movable imaging apparatus 50 of the present embodiment.

First, in step S101, it is decided whether the control unit 32 is connected to the external RIS (Radiology Information System) terminal via the external communication connector 37. When it is decided that the control unit 32 is connected to the RIS terminal, the process advances to step S102. In step 102, for example, management information is captured from the RIS terminal in response to an operation performed on the second operating unit 36 by the operator, and management information including imaging results is outputted to the RIS terminal. Then, in step S103, the management information is displayed as a list in the second operating unit 36.

In this way, the operator (technician) can connect the control unit 32 of the movable imaging apparatus 50 and the RIS terminal of a hospital via the external communication connector 37 and transfer management information including an X-ray imaging order to the imaging apparatus 50. The transferred management information is displayed as a list in the second operating unit 36, so that the technician can confirm the management information. With this display, the operator can make up a rough schedule of imaging for a round of visits in consideration of priority and a route. As shown in FIG. 10A, contents displayed as a list include, for example, patient information such as patient's names and genders, room numbers, and imaging requirements such as imaged parts and imaged postures.

After the preparation is completed, the operator starts moving to a predetermined room according to the schedule while pushing the movable imaging apparatus 50.

When the operator moves the movable imaging apparatus 50, the operator does not operate the X-ray generator 28 or the imaging unit 10 in order to safely move the apparatus. The present embodiment prevents an unnecessary action caused by an unnecessary operation (operations on the X-ray generator 28 and the imaging unit 10) in a moving state, thereby preventing excessive power consumption. For this purpose, the present embodiment has the function of automatically suspending, when the movement of the apparatus is detected, functions not being used in a moving state. This function reduces power consumption in a moving state. As described above, the movable imaging apparatus 50 detects the rotation of the wheel 24 and detects the moving state of the movable imaging apparatus 50. In the present embodiment, when the rotation sensor 25 detects a certain speed, it is decided that the apparatus is in a moving state and functions to be suspended are automatically suspended.

The functions to be suspended are various operation functions including the settings of the X-ray generator 28 and the imaging unit 10. In the present embodiment, the operation function of the first operating unit 34 is suspended. Consequently, it is possible to prevent a malfunction occurring when the driving circuit 30 or the imaging unit 10 is driven by a careless touch on the input device such as an operation key, thereby achieving safety during the movement of the apparatus as well as low power consumption.

In order to make up a schedule of imaging for a round of visits, a list of patient information has to be displayed even in a moving state. As described above, in the second operating unit 36, a list for confirming rooms and patient's names is displayed. Therefore, the second operating unit is caused to act even when the movable imaging apparatus 50 is in a moving state. Thus, the function of displaying a list of patient information and making access to the list (scrolling or the like of a display) is available even when the apparatus is in a moving state.

In order to achieve the above operations, whether the movable imaging apparatus 50 is in a moving state or not is detected based on the detection of the rotation of the wheel 24 in the rotation sensor 25. When a moving state is detected, the processing advances from step S104 to step S109, the first operating unit 34 is suspended, and then the processing returns to step S101.

When the movement of the movable imaging apparatus 50 is completed and a stop is detected by the rotation sensor 25, the processing advances from step S104 to step S105 where the function of the first operating unit 34 is restored. When various imaging settings are made by the first operating unit 34 and the start of imaging is instructed, the processing advances from step S106 to step S107 where the X-ray imaging of the X-ray generator 28 and the imaging unit 10 is started. When X-ray imaging is completed, the processing advances to step S108, corresponding management information is updated, and the processing returns to step S101. Upon updating the management information, for example, "completed" is set for an imaging order, and information for associating a photographed image stored in the storage part with an imaging order is recorded. Thereafter, when a list of displayed management information is updated in step S103, imaged information is reflected on "imaging" columns shown in FIGS. 10A and 10B (the corresponding column is changed from "not completed" to "completed").

For example, when the operator moves the movable imaging apparatus 50 to a predetermined room and stops moving the movable imaging apparatus 50, the first operating unit 34 is made operable (step S105). Thereafter, the operator adjusts the position of the X-ray generator 28 relative to a predetermined imaging posture, selects an imaged part, confirms and sets, through the first operating unit 34, imaging conditions such as the tube voltage (kv), tube current (mA), and exposure time (mS) of the X-ray generator 28, and instructs the start of imaging. X-ray imaging is performed in response to the instruction to start imaging (steps S106 and S107). When X-ray imaging is completed, the completion of imaging is reflected on the management information of the patient, and the management information is automatically updated (step S108).

Then, the updated management information is displayed on the operating unit 36 in step S103, and thus the operator can easily decide whether a subsequent order is placed or not and which room to go. To be specific, when an uncompleted imaging order is found in a displayed list of management information, the operator moves to a subsequent room and repeats X-ray imaging according to the series of operations and processing. When no imaging order is left, the operator returns the movable imaging apparatus 50 to a predetermined standby position. The control unit 32 of the movable imaging apparatus 50 and the RIS terminal of a hospital are connected to each other via the external communication connector 37, and the updated management information can be outputted to the RIS terminal (steps S101 and S102).

Various methods are available for suspending functions including the setting and driving of the X-ray generator 28 and the imaging unit 10. In the first embodiment, since operations for setting and driving the X-ray generator 28 and the imaging unit 10 are performed using the first operating unit 34, the following solution is available: for example, simply power supply to the first operating unit 34 is turned off, or output to the first operating unit 34 (display output including backlight for a liquid crystal display) is turned off and no reaction is allowed to an input operation to the first operating unit 34.

As described above, several effects can be achieved by the separated first and second operating units. For example, the second operating unit 36 is detachably attached to the imaging apparatus body 21, so that the second operating unit 36 can be carried alone by the operator as an information terminal such as a PDA. In this case, it is possible to add, for example, another function of informing the operator about an urgent imaging order or the like. For example, an urgent order can be received and confirmed through radio waves and so on by carrying the terminal in a standby state, or an urgent order can be carried in a separated terminal. Further, monitors can be configured according to specifications such as resolutions required respectively for the first and second operating units 34 and 36. For example, a menu screen for controlling imaging does not require a high resolution. A high resolution increases an amount of data of information including an operation icon. On the other hand, when a list is displayed, it is desirable to output much information on one screen, so that a display with a high resolution is desired. Therefore, it is desirable that the monitor of the first operating unit 34 has a relatively low resolution and the monitor of the second operating unit 36 has a higher resolution.

In the present embodiment, the rotation of the wheel 24 of the carriage 22 is detected using an encoder or the like, so that it is decided whether the apparatus is in a moving state or not. The detection is not limited to the above. For example, a moving state may be decided at the detection of the X-ray generator 28 stored on a predetermined position (e.g., a position described later in the fourth embodiment (FIG. 7)). Alternatively, for example, the release of a braking state of a braking mechanism provided in the carriage 22 may be detected to decide whether the apparatus is in a moving state or not. From these points of view, it is understood that a moving state of the apparatus includes a movable state as well as a state in which the apparatus is actually moving. Moreover, the brake may be released in a mechanical manner or released at the detection of the X-ray generator 28 stored on a predetermined position (for example, when the X-ray generator 28 is stored on a position described later in the fourth embodiment (FIG. 7)). Further, the imaging unit 10 may be detachably attached to the body 21 and the braking state may be released when it is detected that the imaging unit 10 is detached from the body 21. As a matter of course, the apparatus may be decided to be in a moving state when it is detected that the imaging unit 10 is detached from the body 21. When the carriage 22 includes a motor for driving the wheels, the apparatus may be decided to be in a moving state when an instruction to drive the motor is issued.

As described above, according to the first embodiment, a function unused during a movement is suspended, whereas a function useful during a movement keeps working, so that it is possible to reduce standby power consumption without causing any problems in operations and reduce unnecessary power consumption caused by a malfunction.

Second Embodiment

The first embodiment described the configuration in which the first operating unit 34 for setting and driving the X-ray generator 28 and the imaging unit 10 and the second operating unit 36 for displaying management information are separated. The advantages of the separated first and second operating units were already described above. When greater importance is placed on cost than these advantages, the operating units may be configured as a single unit. An example of a second embodiment will describe that a power saving is achieved and an operating error is prevented in such cases.

Figure 4:
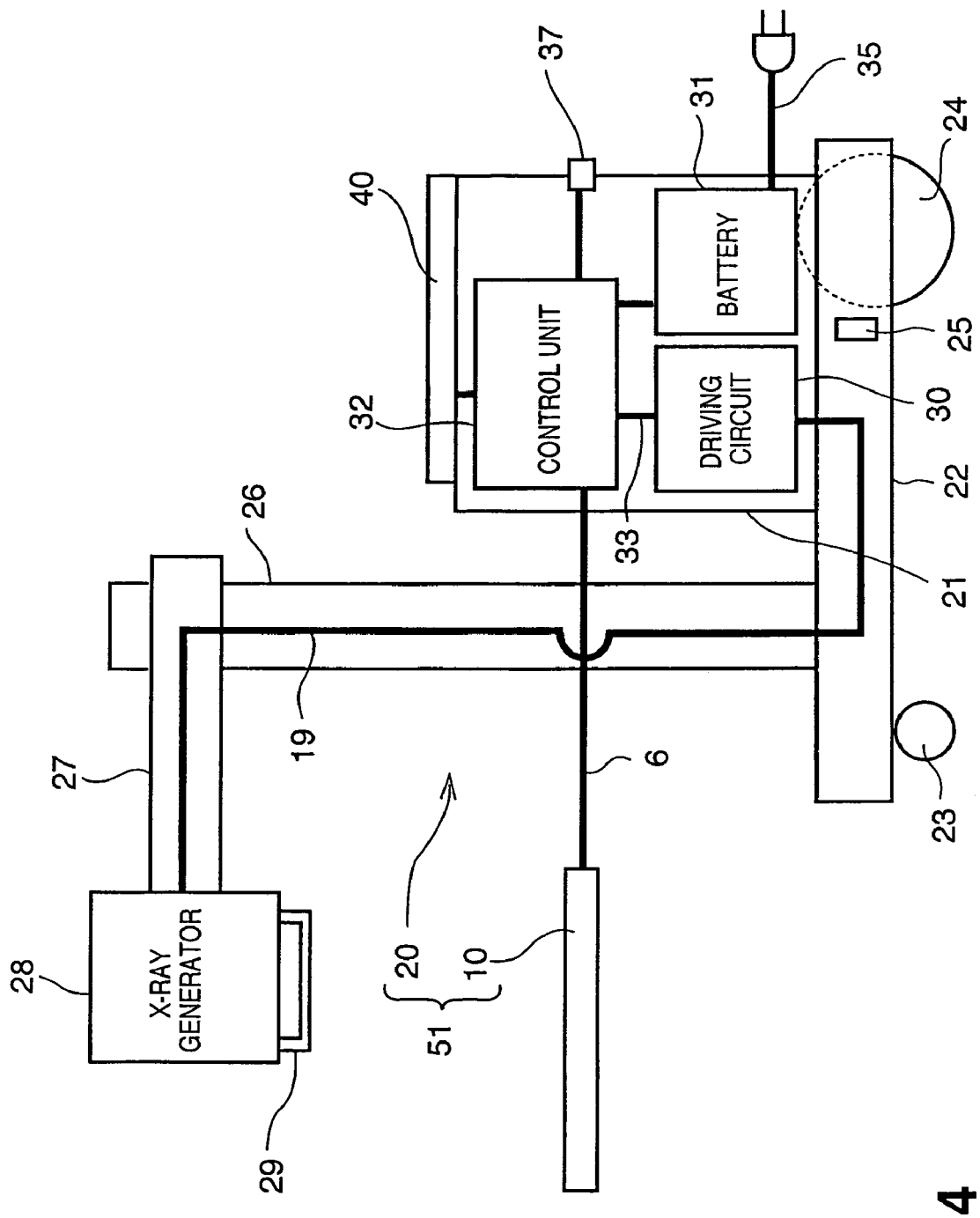
FIG. 4 is a diagram for explaining the configuration of a movable imaging apparatus according to a second embodiment.

FIG. 4 is a schematic structural diagram for explaining the configuration of a movable imaging apparatus 51 according to the second embodiment. The second embodiment is similar to the first embodiment except that the first operating unit 34 and the second operating unit 36 of the first embodiment are configured as one operating unit 40. The operating unit 40 has a display device as an output unit and a touch panel on the display device as an input unit. The functions of the first and second operating units 34 and 36 of the first embodiment are implemented by switching screens on the display device.

Figure 5A:
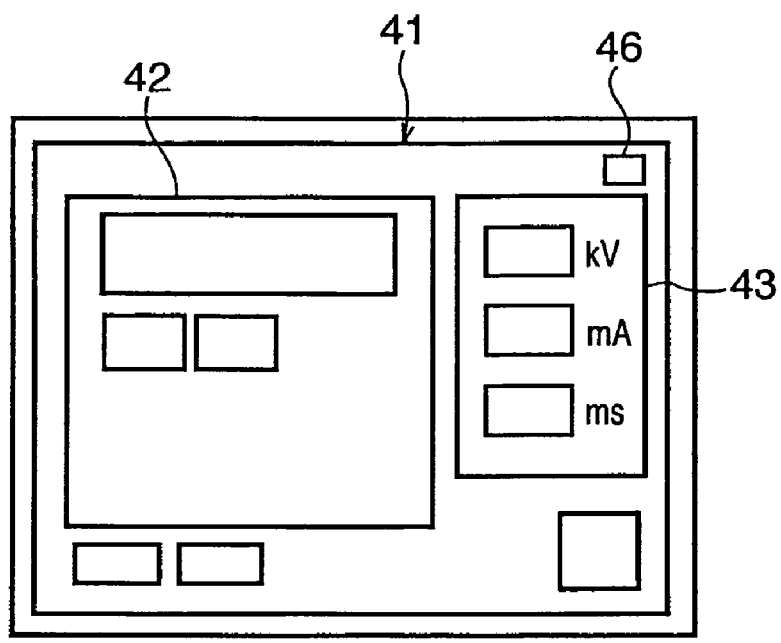
FIGS. 5A and 5B are diagrams for explaining the screen configuration of an operating unit according to the second embodiment.
Figure 5B:
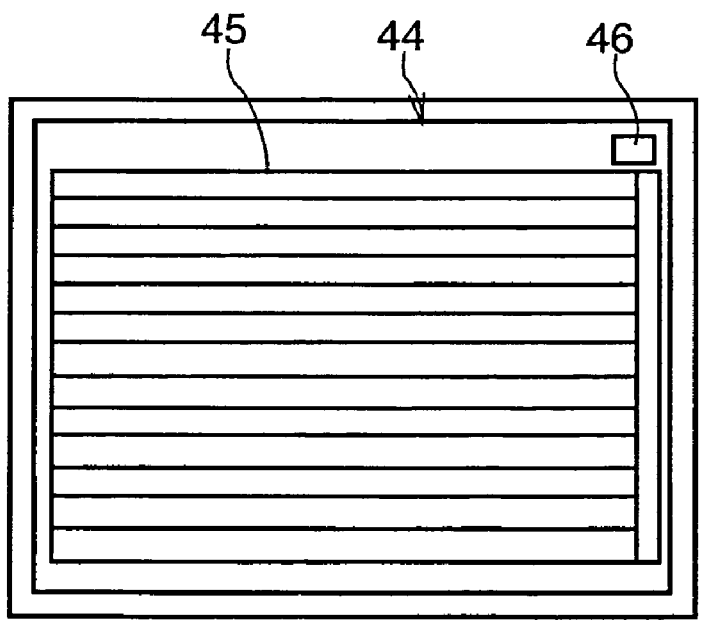

FIGS. 5A and 5B show display examples of the display device of the second embodiment. As shown in FIG. 5A, a first screen 41 has an operation area 42 for selecting an imaged part and an operation area 43 for confirming/setting the imaging conditions of an X-ray generator 28 and/or an imaging unit 10. As shown in FIG. 5B, a list 45 of patient information and imaging requirements (for example, a list of FIG. 10A based on management information) is displayed on a second screen 44. The screens can be alternately switched by selecting a screen switch key 46.

When it is detected that the movable imaging apparatus 51 is in a moving state, a screen is automatically switched to the second screen 44 and the screen switch key 46 is disabled, so that switching to the first screen 41 cannot be performed. A moving state is detected, for example, based on a signal from a rotation sensor 26. Thus, as in the first embodiment, an operation (operating error) on the X-ray generator 28 and the imaging unit 10 can be prevented during a movement, thereby achieving lower power consumption.

Third Embodiment

In the second embodiment, when the apparatus is in a moving state, an operating error is prevented by switching the screens with the single operating unit 40. In a third embodiment, one screen is divided into two or more areas one of which does not accept an operation input when a movable imaging apparatus is in a moving state, thereby preventing an operating error.

Figure 6:
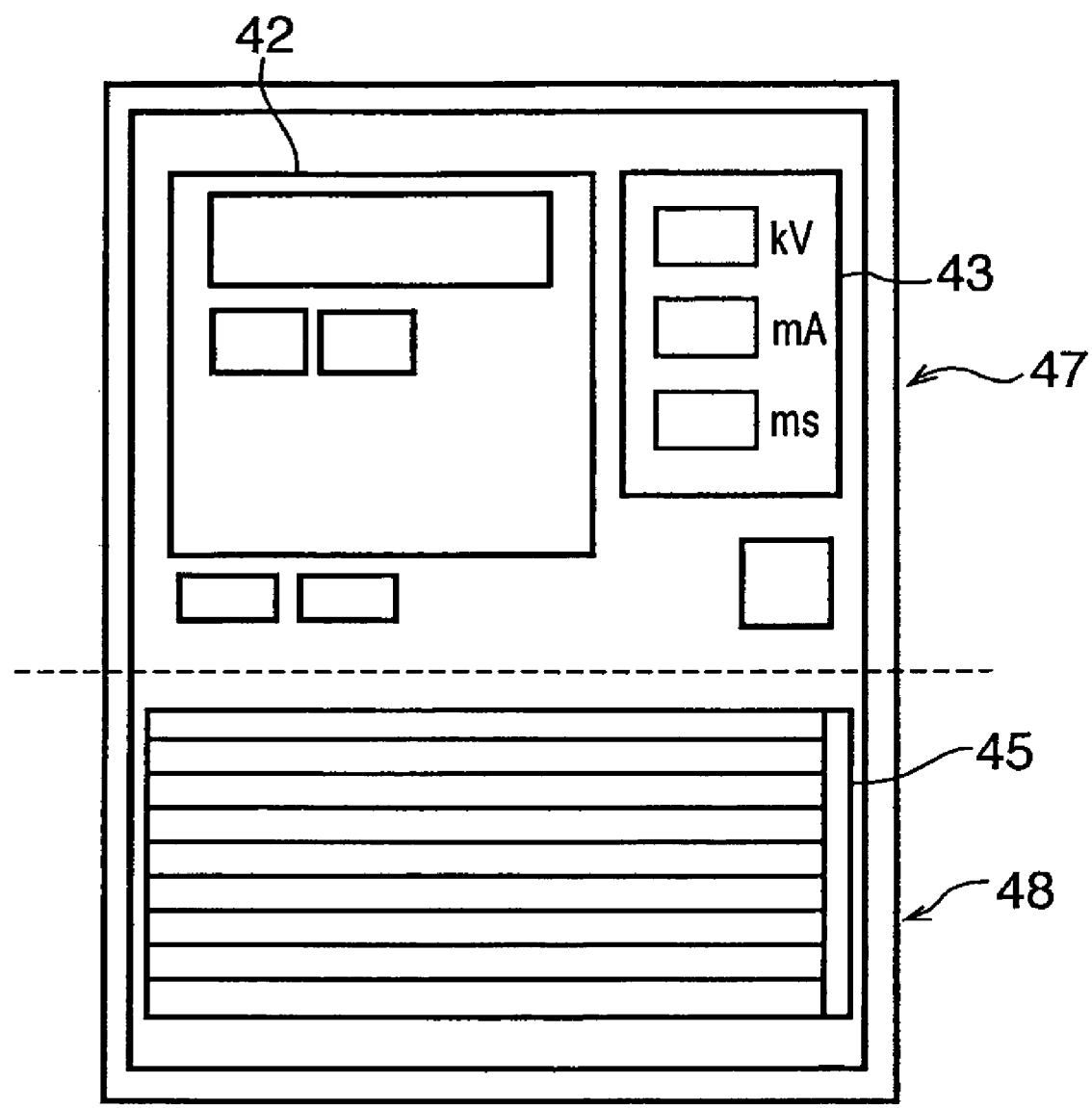
FIG. 6 is a diagram for explaining the screen configuration according to a third embodiment.

FIG. 6 is a diagram showing a display example of an input/output device 40 of the third embodiment. In the example of FIG. 6, a screen on a display device is divided into a display area 47 and a display area 48. The display area 47 displays a screen for operating an X-ray generator 28 and an imaging unit 10 and the display area 48 displays a list of patient information (list display in FIG. 10A) based on management information. When a movement of the movable imaging apparatus is detected, output to the first display area is automatically turned off to prevent reaction to input. Only the display area 47 may act as an area not reacting to input. With this configuration, the apparatus reacts to input to the display area 48, so that the apparatus can react when scrolling is necessary in the display of a list of patient information.

Fourth Embodiment

Figure 7:
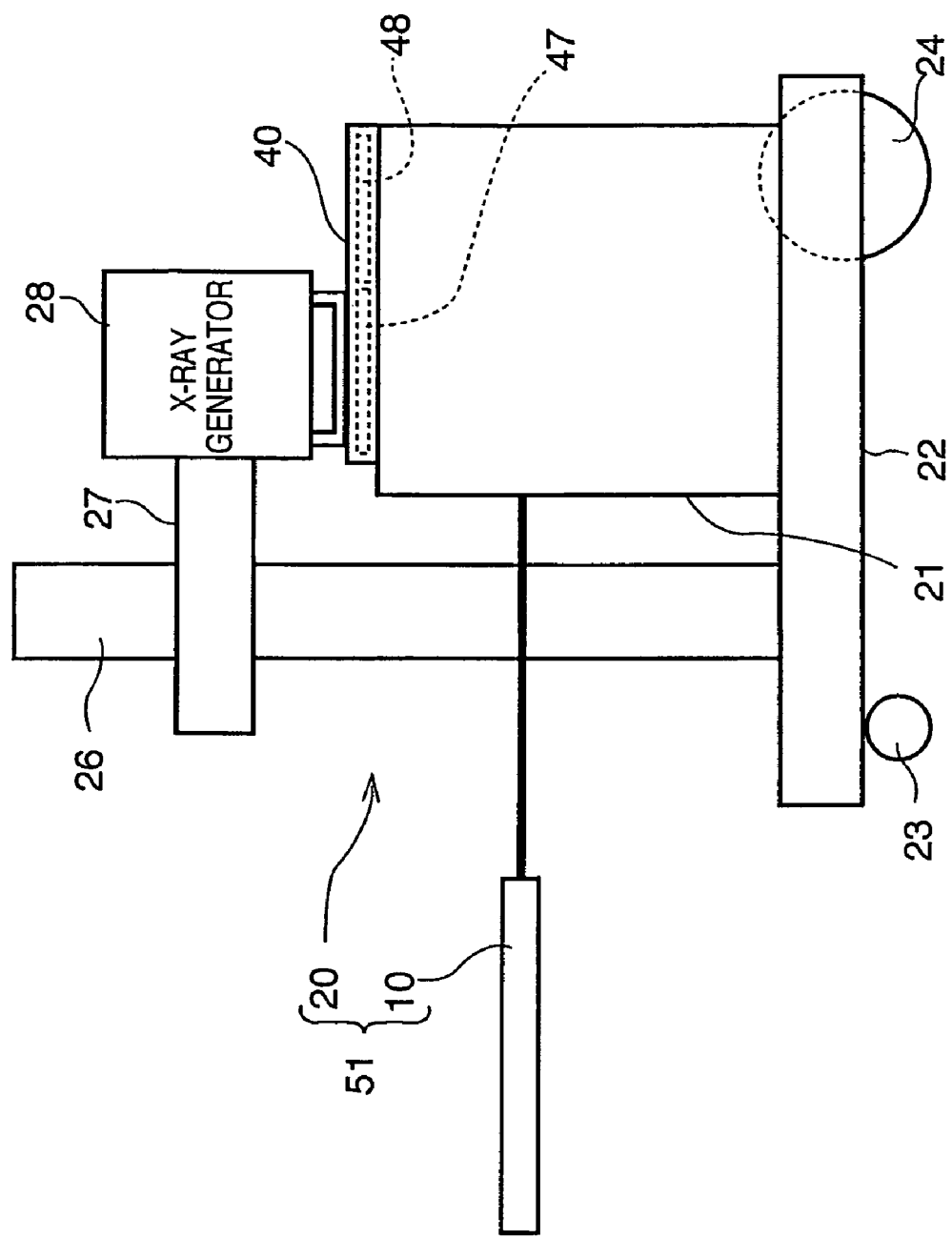
FIG. 7 is a diagram for explaining a movable imaging apparatus according to a fourth embodiment.

A fourth embodiment of FIG. 7 is similar to the third embodiment in the configuration of input/output means, but a suspending method is different. During a movement, it is desirable to return an X-ray generator to a predetermined position for safety. For this purpose, the X-ray generator 28 is stored above an imaging apparatus body 21 so as to hide a divided first display area 47 but so as not to hide a second display area 48. Thus, physical access cannot be made to the first display area 47, thereby achieving the function of preventing an accidental operation. Additionally, the imaging apparatus has means for detecting the X-ray generator on a predetermined storage position. When the X-ray generator is not on the predetermined position, the imaging apparatus is prohibited from moving. Therefore, the first display area 47 can be positively hidden by the X-ray generator during a movement.

In the present embodiment, it is detected that the X-ray generator 28 is stored on the above position, a braking state of a braking mechanism provided on a carriage 22 is released in response to the detection, and the apparatus becomes movable.

The above explanation described a single operating unit. The same method is applicable to first and second operating units separated as the first embodiment. In this case, for example, the storage position of the X-ray generator 28 is set such that only the first operating unit 34 is hidden and the second operating unit 36 is not hidden. Instead of hiding the first operating unit with the X-ray generator, the second operating unit having been separately formed may slide onto the first operating unit so as to hide the first operating unit. In this case, a braking state is released when it is detected that the second operating unit is disposed on the first operating part.

Fifth Embodiment

Figure 8:
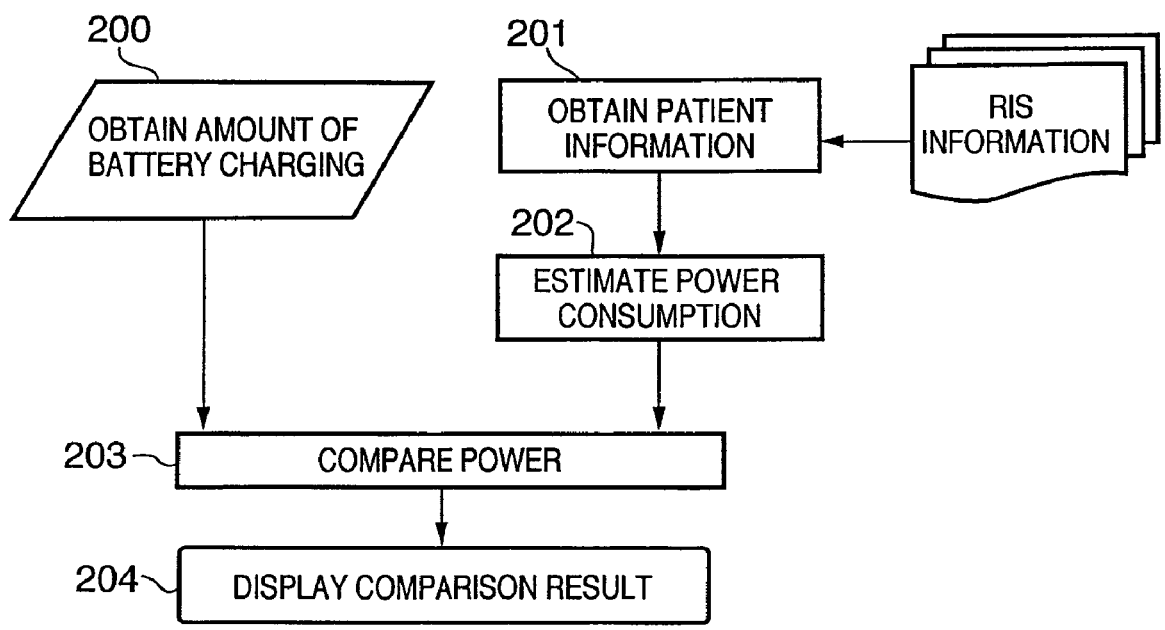
FIG. 8 is a diagram for explaining a movable imaging apparatus according to a fifth embodiment.
Figure 9:
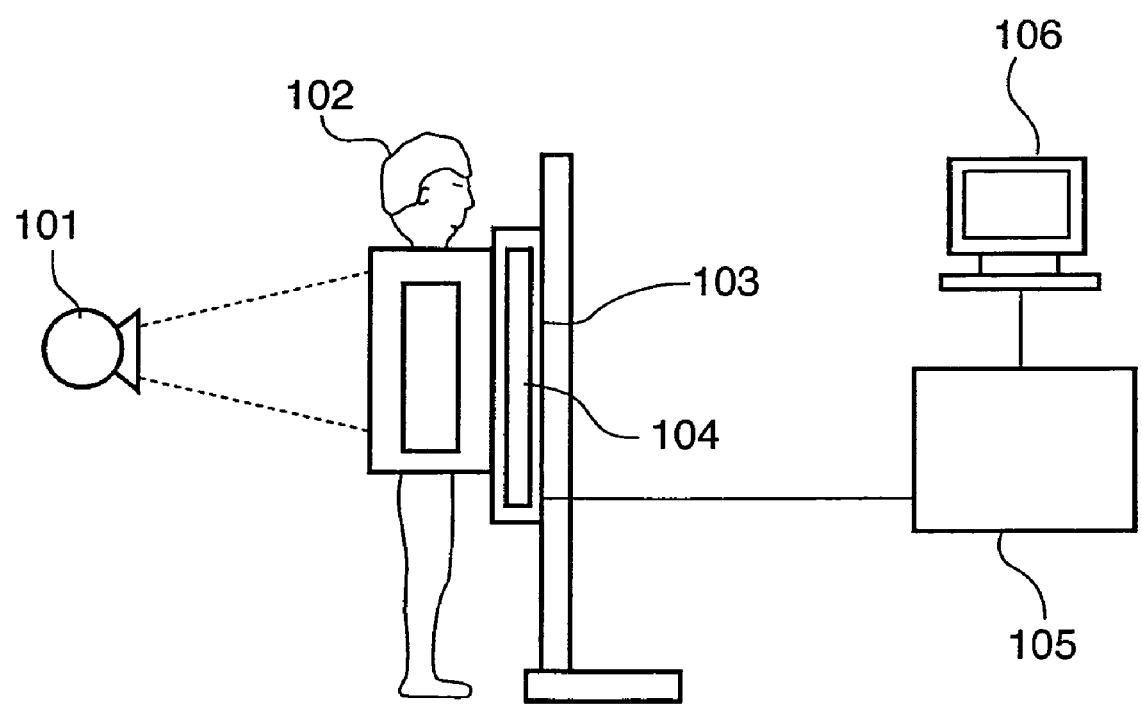
FIG. 9 is a diagram for explaining a typical radiation imaging system.

It is necessary to avoid a situation in which a dead battery interferes with imaging during a round of visits. For this reason, it is desirable to have the function of monitoring beforehand power charged for imaging in an imaging apparatus. That is, in addition to solutions for reducing power consumption as described above, it is desired to provide notification of power consumption required for subsequent imaging and provide notification of whether a current charging state can afford the power consumption. A fifth embodiment will describe an imaging apparatus capable of providing such notification. The configuration of the movable imaging apparatus is identical to that of the first embodiment (FIGS. 1 and 2). Referring to FIG. 8, the following will discuss the provision of a notification about the power of the movable imaging apparatus according to the fifth embodiment.

First, when management information including an imaging order is captured from an RIS terminal to a movable imaging apparatus 50, information on patients (patient information) for whom imaging is ordered is obtained from the management information (step 201). Since the captured management information includes a tube voltage, a tube current, and an irradiation time as imaging requirements, the power consumption of an X-ray generator 28 can be calculated for each imaging order. Power consumptions are calculated and summed for all imaging orders, so that the total power consumption is calculated. A time period during which an X-ray detection panel 1 of an imaging unit 10 is driven is determined by calculating an irradiation time, and thus power consumption required by the imaging unit 10 can be also calculated. By adding power consumed by a control unit 32 and first and second operating units 34 and 36 to these power consumptions, the overall power consumption can be estimated (step 202).

The control unit 32 monitors a charging state of a battery 31 (step 200) and compares the power consumption estimated in step 202 and power charged in the battery 31 (step 203). Thus, it is possible to decide whether a charging state is sufficient for ordered imaging and notify the operator about this information (step 204). A way to notify the operator of this information includes (1) simply displaying percentages relative to power required for an imaging order as numeric values or a graph or (2) marking acceptable orders on a list displayed on a second operating unit 36. For example, as shown in FIG. 10B, whether imaging is possible or not may be displayed on a list.

As described above, according to the fifth embodiment, a necessary battery capacity is estimated based on imaging orders received from management information and compared with a current battery capacity, so that the operator can be notified of the excess or deficiency of charge. Hence, an efficient operation can be obtained. For example, a schedule of imaging can be adjusted beforehand.

According to the present invention, it is possible to suspend an unnecessary function to reduce the occurrence of an unnecessary operation caused by an operating error or the like when an apparatus is in a moving state and, in turn, to reduce power consumption.

It is needless to say that the X-ray imaging apparatuses of the foregoing embodiments can be modified in various manners without departing from the scope of the claims.

As many apparently widely different embodiments of the present invention can be made without departing from the spirit and scope thereof, it is to be understood that the invention is not limited to the specific embodiments thereof except as defined in the appended claims.

What is claimed is:

1. A radiation imaging apparatus comprising:
   a dolly configured to mount and carry a radiation generator, an imaging unit to obtain a radiation image, and an operating unit to provide an interface to a user, wherein the dolly makes the radiation imaging apparatus movable;
   an obtaining unit configured to obtain an amount of electric power needed for imaging based on management information including an imaging order; and
   a notification unit configured to compare the amount of electric power obtained by the obtaining unit and a remaining amount of charge of a battery for supplying power to the apparatus, and provide notification of a result.

2. The apparatus according to claim 1, wherein said notification unit determines a possible imaging order based on the comparison result out of imaging orders included in the management information, and provides notification of the possible imaging order.

3. A method of controlling a radiation imaging apparatus having a radiation generator, an imaging unit to detect a radiation image data, and a dolly for carrying the radiation generator and the imaging unit, wherein the dolly makes the radiation imaging apparatus movable, the method comprising:
   an obtaining step of obtaining an amount of electric power needed for imaging based on management information including an imaging order; and
   a notifying step of comparing the amount of electric power obtained in the obtaining step and a remaining amount of charge of a battery for supplying power for the method, and providing notification of a result.

4. The method according to claim 3, wherein in the notifying step, a possible imaging order is determined based on the comparison result out of imaging orders included in the management information, and notification of the possible imaging order is provided.

* * * * *